US007005143B2

(12) United States Patent
Abuelyaman et al.

(10) Patent No.: US 7,005,143 B2
(45) Date of Patent: Feb. 28, 2006

(54) GEL MATERIALS, MEDICAL ARTICLES, AND METHODS

(75) Inventors: Ahmed S. Abuelyaman, Woodbury, MN (US); Scott A. Burton, Woodbury, MN (US); Duane Fansler, Dresser, WI (US); Babu N. Gaddam, Woodbury, MN (US); Paul Hattam, Baldwin, WI (US); Maureen A. Kavanagh, Stanchfield, MN (US); Kevin M. Lewandowski, Inver Grove Heights, MN (US); Peter M. Seiler, Minneapolis, MN (US); Steven C. Stickels, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 320 days.

(21) Appl. No.: 10/121,518

(22) Filed: Apr. 12, 2002

(65) Prior Publication Data

US 2003/0203011 A1    Oct. 30, 2003

(51) Int. Cl.
*A61K 9/14*     (2006.01)
*A61K 31/74*    (2006.01)
*C08F 120/00*   (2006.01)

(52) U.S. Cl. .................. 424/487; 424/78.17; 525/329.5
(58) Field of Classification Search ............... 424/487, 424/78.17; 525/329.5
See application file for complete search history.

(56) References Cited

U.S. PATENT DOCUMENTS

| RE24,906 E | 12/1960 | Ulrich |
|---|---|---|
| 3,121,021 A | 2/1964 | Copeland |
| 3,389,827 A | 6/1968 | Abere et al. |
| 4,112,213 A | 9/1978 | Waldman |
| 4,424,311 A | 1/1984 | Nagaoka et al. |
| 4,499,896 A | 2/1985 | Heinecke |
| 4,538,603 A | 9/1985 | Pawelchak et al. |
| 4,554,297 A | 11/1985 | Dabi .......................... 521/178 |
| 4,598,004 A | 7/1986 | Heinecke |
| 4,738,257 A | 4/1988 | Meyer et al. |
| 4,798,604 A | 1/1989 | Carter |
| 4,840,851 A | 6/1989 | Gölander et al. |
| 4,849,458 A | 7/1989 | Reed et al. |
| 4,909,243 A | 3/1990 | Frank et al. |
| 4,909,244 A | 3/1990 | Quarfoot et al. |
| 4,935,087 A | 6/1990 | Gilman |
| 4,979,946 A | 12/1990 | Gilman |
| 5,018,515 A | 5/1991 | Gilman |
| 5,059,424 A | 10/1991 | Cartmell et al. |
| 5,064,652 A | 11/1991 | Bay |
| 5,088,483 A | 2/1992 | Heinecke |
| 5,254,723 A | 10/1993 | Yang et al. |
| 5,328,450 A | 7/1994 | Smith et al. |
| 5,429,590 A | 7/1995 | Saito et al. |
| 5,455,027 A | 10/1995 | Zalipsky et al. ......... 424/78.17 |
| 5,468,821 A | 11/1995 | Lucast et al. |
| 5,514,380 A * | 5/1996 | Song et al. ................. 424/426 |
| 5,531,855 A | 7/1996 | Heinecke et al. |
| 5,603,946 A | 2/1997 | Constantine |
| 5,614,310 A | 3/1997 | Delgado et al. |
| 5,653,699 A | 8/1997 | Reed et al. |
| 5,733,570 A | 3/1998 | Chen et al. |
| 5,738,642 A | 4/1998 | Heinecke et al. |
| 5,783,209 A | 7/1998 | Imamura et al. |
| 5,849,325 A | 12/1998 | Heinecke et al. |
| 5,932,200 A | 8/1999 | Reich et al. |
| 5,941,840 A | 8/1999 | Court et al. |
| 6,165,408 A | 12/2000 | Steinmann .................. 264/496 |
| 6,171,985 B1 | 1/2001 | Joseph et al. |
| 6,198,016 B1 | 3/2001 | Lucast et al. |
| 6,353,069 B1 * | 3/2002 | Freeman et al. ............ 526/319 |
| 2002/0188277 A1 * | 12/2002 | Roorda et al. .............. 604/523 |
| 2003/0044468 A1 * | 3/2003 | Cellesi et al. ............... 424/487 |
| 2003/0152623 A1 * | 8/2003 | Bromberg et al. .......... 424/468 |
| 2004/0002456 A1 * | 1/2004 | Pathak ........................ 514/12 |

FOREIGN PATENT DOCUMENTS

| EP | 0 269 071 B1 | 6/1988 |
|---|---|---|
| JP | SHO 59-7687 | 2/1984 |

(Continued)

(Continued)

OTHER PUBLICATIONS

Technical Bulletin, Pluronic® Block Copolymer NF Grade (Poloxamer NF Grades), BASF Corporation, Mount Olive, New Jersey (1995) (2 pgs).

(Continued)

*Primary Examiner*—Tatyana Zalukaeva
(74) *Attorney, Agent, or Firm*—Cheree H. Johnson

(57) ABSTRACT

A gel material and medical articles including such material, wherein the transparent gel material includes a polymerized poly(alkylene oxide) macromonomer that, prior to polymerization, is free-radically polymerizable, multifunctional (preferably difunctional), and has an average molecular weight of at least about 2000.

25 Claims, 1 Drawing Sheet

FOREIGN PATENT DOCUMENTS

| | | |
|---|---|---|
| JP | HEI 10/158621 | 6/1998 |
| WO | WO 84/03837 | 10/1984 |
| WO | WO 97/05185 | 2/1997 |
| WO | WO 97/11658 | 4/1997 |
| WO | WO 97/42917 | 11/1997 |
| WO | WO 98/17328 | 4/1998 |
| WO | WO 99/06077 | 2/1999 |
| WO | WO 99/13865 | 3/1999 |
| WO | WO 99/13866 | 3/1999 |
| WO | WO 00/14131 | 3/2000 |
| WO | WO 00/42958 | 7/2000 |
| WO | WO 01/41687 A1 | 6/2001 |
| WO | WO 01/60296 A1 | 8/2001 |
| WO | WO 02/20067 A2 | 3/2002 |

OTHER PUBLICATIONS

ASTM D1003-00, "Standard Test Method for Haze and Luminous Transmittance of Transparent Plastics," *Annual Book of ASTM Standards*, vol. 08.01, pp. 201-206 (2002).

* cited by examiner

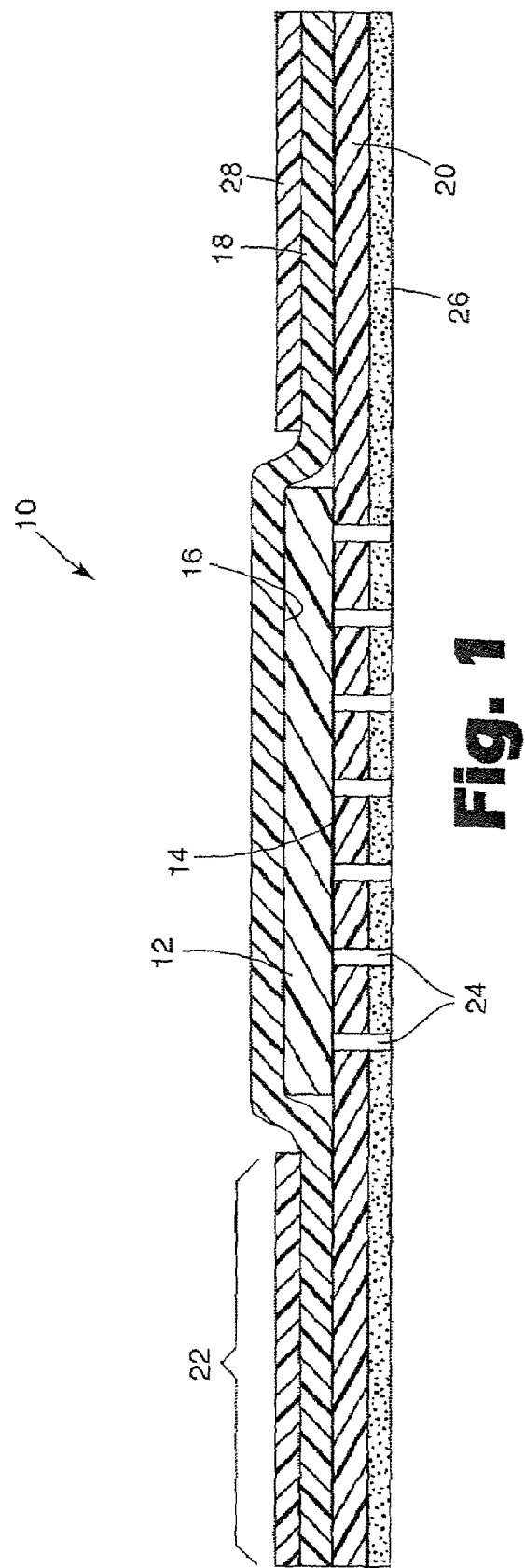

GEL MATERIALS, MEDICAL ARTICLES, AND METHODS

BACKGROUND

The present invention is directed to gel materials and medical articles incorporating such materials, particularly medical articles useful as wound dressings. More particularly this invention is directed to gel materials prepared from a multifunctional poly(alkylene oxide) macromonomer.

Historically, exudate from a wound has been treated by absorbing it using a dressing containing an absorbent material. Typical such dressings contain a padded absorbent material attached to an adhesive tape backing. The padded absorbent material is applied to the wound to absorb the wound exudate. A difficulty with this type of dressing is that the scab typically forms in and as part of the pad as the wound heals. Thus, when the dressing is removed, the scab is removed. This problem has been addressed by providing a porous film between the absorbent material and the wound to reduce the likelihood that a scab formed will become attached to the absorbent material.

More recently the use of so-called "occlusive" dressings for pressure sores and ulcers has gained increasing acceptance. A number of wound dressings of this kind are commercially available. Most of these products are formed from several layers, including at least an inner skin-contacting layer and an outer backing layer. The dressing is applied as a cover for the sore or ulcer in a size providing a margin around the wound area that adhesively seals to the skin. The inner layer contains water-absorptive materials, so that fluid from the wound is absorbed into the layer, making it possible to keep the dressing in place for at least several days. Such occlusive dressings tend to promote healing by maintaining the wound under moist conditions without forming a crust, and serving as a barrier against bacterial infection. Such dressings for "moist wound healing" are particularly useful for dermal burns, traumatic skin deficiencies, incised wounds, and the like.

A wound care product in current use utilizes a hydrocolloid absorbent. Such a material typically has poor transparency so the treatment state cannot be observed from the outside. Also, such a material can partially lose its integrity after absorbing wound fluid. Flexibility of hydrocolloid dressings can be poor, which makes it difficult to apply the dressing to a bend portion of a body, such as a joint, etc. The portion of the absorbent in contact with the wound is converted to a gel-like material, and, when the dressing is removed, a portion of this absorbent material can be left in the wound, and must be removed to permit examination and/or before applying another dressing.

There are known hydrophilic gel materials useful in medical applications such as wound dressings, however, many of them do not have the appropriate balance of absorption and cohesive strength often needed. Thus, additional such materials are needed. Furthermore, it be desirable to provide an occlusive material that is also transparent and flexible for use in a medical article such as a wound dressing or wound packing material.

SUMMARY OF THE INVENTION

This invention provides medical articles and polymeric gel materials for use therein, which are preferably absorbent, and more preferably absorbent and transparent. By "gel" (or "polymer gel" or "polymeric gel material" or "hydrophilic gel") it is meant a gel material capable of swelling on contact with (or water-based fluids such as body fluids including blood, plasma, and intracellular fluid or fluids similar to body fluids such as physiological saline), but does not dissolve in, water. The gels are substantially continuous, i.e., lacking a cellular or void stucture (although minor defects such as entrapped air bubbles or fractures may be present) and thus generally in a solid or semi-solid form. The term "gel" is used regardless of the state of hydration. Preferably, the gel does not include water until it comes in contact with a surface from which it absorbs water (e.g., a wound). Significantly, even without water (or other plasticizing agents) preferred embodiments of the gel material of the present invention are flexible.

By "absorbent" it is meant that the material is preferably capable of absorbing fluids, particularly body fluids and preferably moderate to heavy amounts of body fluids, while retaining its structural integrity (i.e., remaining sufficiently intact such that it can perform the function of acting as an absorbent moist wound healing dressing, for example), and preferably its transparency. By "transparent" it is meant that when the preferred material is applied to a patient (e.g., at a wound site), the area underlying the dressing can be visualized sufficiently to permit observation of the wound by a health care worker.

The application of water swelling polymer gels to medical practice is, for example, found in wound dressings, wound packings, adhesives (particularly pressure sensitive adhesives), contact lenses, intraocular lenses, adhesives for biological tissues, adhesion preventing materials, adsorbents for blood purification, base materials for releasing pharmacologic agents, and the like. Materials for dental moldings or impressions are another potential medical article use. Thus, as used herein, "medical" applications encompasses dental applications, including dental adhesives, restoratives, coatings, composites, sealants, etc. Because water swelling polymer gels have compositions and mechanical properties similar to those of biological tissues, such gels may be applied in a wide variety of fields in the future.

In one embodiment, the present invention provides a medical article that includes a gel material including a homopolymer or copolymer of a multifunctional poly(alkylene oxide) free-radically polymerizable macromonomer having a weight average molecular weight of at least about 2000, wherein the multifunctional poly(alkylene oxide) macromonomer comprises a copolymeric random alkylene oxide moiety of the formula:

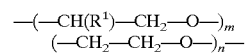

wherein the mole ratio of m:n is within a range of about 1:9 to about 9:1; and $R^1$ is a (C1–C4)alkyl group. In this representation, there is a relatively random structural distribution of —CH($R^1$)—CH$_2$—O— moieties and —CH$_2$—CH$_2$—O— moieties.

The present invention also provides a preferred embodiment of a medical article, preferably a wound dressing, that includes a facing layer (preferably, a fluid permeable facing layer) and a backing layer (preferably, a moisture vapor permeable backing layer) with the gel material (typically in the form of a layer) disposed between the two. Preferably the backing layer is both moisture vapor permeable and liquid impermeable. The medical article, e.g., wound dressing, may further include a layer of pressure sensitive adhesive to secure the article to the skin.

As used herein the terms "front surface" and "back surface" used with respect to the gel layer, the facing layer, and the backing layer, refer to the major surface of the indicated layer that, in use, faces toward the wound surface or away from the wound surface, respectively.

That is, the gel material of the present invention, which is preferably absorbent and transparent, includes a polymerized poly(alkylene oxide) macromonomer that, prior to polymerization, is free-radically polymerizable, multifunctional (preferably difunctional), and has an average molecular weight of at least about 2000 (preferably at least about 4000, and more preferably at least about 6000). This gel material can be a homopolymer of the multifunctional macromonomer, or it can be a copolymer (i.e., having two or more different monomers), wherein at least one of the monomers is a multifunctional macromonomer of the above formula. Other monomers that can be copolymerized with the multifunctional macromonomer include, for example, monofunctional poly(alkylene oxide) monomers, polar monomers, and hydrophobic monomers.

In one preferred embodiment, the present invention provides a medical article that includes a gel material, which is preferably absorbent, and more preferably absorbent and transparent. The gel material includes a copolymer prepared from monomers including: a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

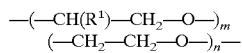

wherein the mole ratio of m:n is within a range of about 1:9 to about 9: 1; and $R^1$ is a (C1–C4)alkyl group; a monofunctional poly(alkylene oxide) monomer; and a polar monomer. As used herein, "a" or "an" mean "at least one" or "one or more" unless specifically indicated otherwise.

In one preferred embodiment, the present invention provides a medical article that includes a gel material, which is preferably absorbent, and more preferably absorbent and transparent. The gel material includes a homopolymer or copolymer prepared from monomers including: about 5 wt-% to 100 wt-% of a multifunctional poly(alkylene oxide) free-radically polymerizable macromonomer having a weight average molecular weight of at least about 2000, wherein the multifunctional poly(alkylene oxide) macromonomer comprises a copolymeric alkylene oxide moiety of the formula:

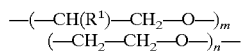

wherein the mole ratio of m:n is within a range of about 1:9 to about 9:1; and $R^1$ is a (C1–C4)alkyl group; 0 wt-% to about 80 wt-% of a monofunctional poly(alkylene oxide) monomer; and 0 wt-% to about 40 wt-% of a polar monomer.

Polymers of the present invention are prepared from preferred macromonomers. In one embodiment, a preferred multifunctional macromonomer is provided that includes a copolymeric random alkylene oxide moiety of the formula:

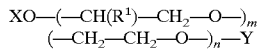

wherein the mole ratio of m:n is within a range of about 1:9 to about 9: 1, $R^1$ is a (C1–C4)alkyl group, and X and Y are independently selected from the group consisting of

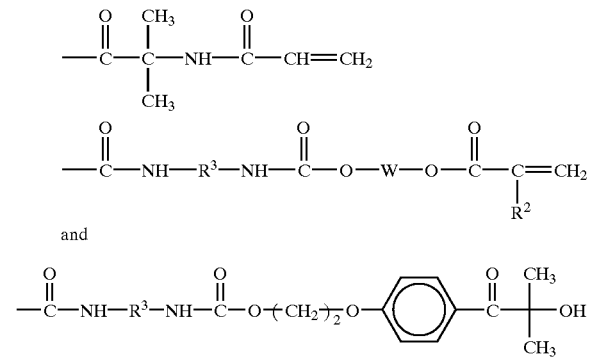

and wherein $R^2$ is H or $CH_3$ (i.e., "Me"), $R^3$ is an aromatic group, aliphatic group, alicyclic group, or combinations thereof, and W is an alkylene or alkylene oxide group.

In another preferred embodiment, a multifunctional macromonomer includes a copolymeric random alkylene oxide moiety of the formula:

XO—(—CH($R^1$)—$CH_2$—O—)$_m$
(—$CH_2$—$CH_2$—O—)$_n$—Y wherein the mole ratio of m:n is within a range of about 1:9 to about 9: 1, $R^1$ is a (C1–C4)alkyl group, and X and Y are independently selected from the group consisting of

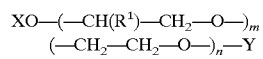

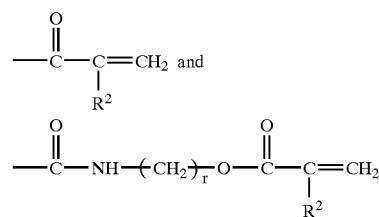

wherein $R^2$ is H or Me and r=2–10.

In another preferred embodiment, a multifunctional macromonomer includes a copolymeric random alkylene oxide moiety of the formula:

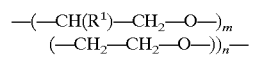

wherein the mole ratio of m:n is within a range of about 1:9 to about 9:1 and $R^1$ is a (C1–C4)alkyl group, and wherein the macromonomer further includes two or more end groups selected from the group consisting of

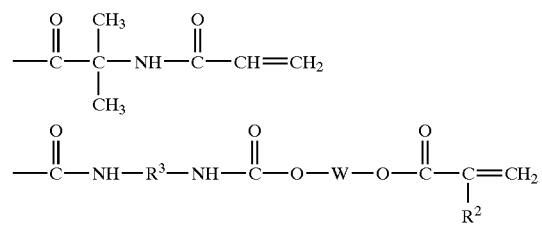

-continued

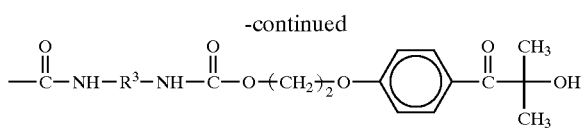

and mixtures thereof, wherein $R^2$ is H or $CH_3$, $R^3$ is an aromatic group, aliphatic group, alicylic group, or combinations thereof, and W is an alkylene or alkylene oxide group.

In another preferred embodiment, a multifunctional macromonomer includes a copolymeric random alkylene oxide moiety of the formula:

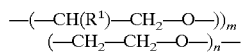

wherein the mole ratio of m:n is within a range of about 1:9 to about 9:1 and $R^1$ is a (C1–C4)alkyl group, and wherein the macromonomer further includes two or more end groups selected from the group consisting of

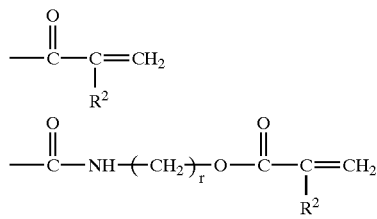

and mixtures thereof, wherein $R^2$ is H or Me and r=2–10.

The present invention also provides a syrup polymer mixture that includes a partially polymerized homopolymer or copolymer prepared from monomers including: about 0.1 wt-% to 100 wt-% of a multifunctional poly(alkylene oxide) free-radically polymerizable macromonomer having a weight average molecular weight of at least about 2000, wherein the multifunctional poly(alkylene oxide) macromonomer includes a copolymeric alkylene random oxide moiety of the formula:

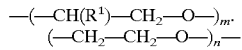

wherein the mole ratio of m:n is within a range of about 1:9 to about 9:1; and $R^1$ is a (C1–C4)alkyl group; 0 wt-% to about 80 wt-% of a monofunctional poly(alkylene oxide) monomer; 0 wt-% to about 40 wt-% of a polar monomer; and 0 wt-% to about 20 wt-% of a hydrophobic monomer. The present invention also provides a method of making a gel, the method includes forming a syrup polymer mixture as described above; and forming a gel from the syrup polymer mixture.

BRIEF DESCRIPTION OF THE FIGURES

FIG. 1 is a cross-section of a wound dressing of the invention.

DETAILED DESCRIPTION OF THE FIGURES

The gel material of the present invention can be used in medical articles. Preferably, the gel material is absorbent.

Preferably, the gel material of the present invention is advantageously transparent, which allows for inspection of an underlying material. Significantly, for medical articles, particularly wound dressings, this allows for visual inspection of the wound without removal of the wound dressing. More preferably, the gel material is both absorbent and transparent.

Preferred medical articles, particularly wound dressings, of the present invention advantageously: can remove excess exudate from the wound; maintain a moist wound environment; allow gas exchange so that oxygen, water vapor, and carbon dioxide can pass through the article; are thermally insulating to maintain the wound at body temperature; may be impermeable to liquids and microorganisms to minimize contamination and infection; may be non-adherent to the wound so that no damage is done to the granulating tissue; and minimize the need to cleanse the wound of dressing material.

The material is preferably absorbent in that it is capable of absorbing fluids, preferably moderate to heavy amounts of fluids such as body fluids, while retaining its structural integrity (and preferably its transparency). Preferably, herein, "absorbent" refers to a material that will absorb at least its own weight of an isotonic saline solution (0.9 wt-% sodium chloride in deionized water) after 24 hours at room temperature. That is, the material has an absorbency of at least 100%. More preferably, the gel material can absorb at least two times its weight (200% absorbency), even more preferably at least four times its weight (400% absorbency), and most preferably at least five times its weight (500% absorbency) of an isotonic saline solution after 24 hours at room temperature. Typically, gel material of the present invention can absorb up to eight times its weight of an isotonic saline solution.

Preferably, the gel material of the present invention is transparent whether dry or swollen with an aqueous solution (e.g., bodily fluid). Preferably, herein, transparent refers to a material having a total light transmittance of greater than 84% per ASTM D 1003-00.

Preferred gel materials of the present invention are also be relatively flexible. Flexibility allows for a medical article incorporating the gel material to be easily applied to a bend portion of a body, such as a joint, etc. Nonflexible gel materials are also within the scope of the present invention. Such gel materials can be used as wound packing materials, for example.

The gel material of the present invention is also preferably biocompatible. Herein, "biocompatible" means that the material can be in contact with bodily tissues (including fluids) without adverse reactions. Typically, this occurs if the residual monomers used to prepare the polymer used in the gel material are present in less than about 1 percent by weight (wt-%) each, based on the total weight of the polymer.

The gel material of the present invention can also possess pressure sensitive adhesive properties. The pressure sensitive adhesives of the invention are polymers exhibiting a glass transition temperature of less than −15° C.

Preferably, the polymer used in the gel material of the present invention is inherently bacteriostatic and possesses low odor. Alternatively, bacteriostatic or odor removing agents can be added to the polymer to enhance these properties of the gel material. Such materials are described in greater detail below.

The gel material of the present invention includes a polymer, which can be a homopolymer or a copolymer, of a multifunctional poly(alkylene oxide) free-radically polymerizable macromonomer. The multifunctional poly(alkylene oxide) macromonomer has a weight average molecular weight of at least about 2000. Preferably, the multifunctional poly(alkylene oxide) macromonomer includes a copolymeric alkylene oxide moiety of the formula (Formula I):

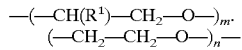

wherein the mole ratio of m:n is within a range of about 1:9 to about 9:1 (preferably, within a range of about 1:5 to about 1:1); and $R^1$ is a (C1–C4)alkyl group, which can be linear or branched. The distribution of the alkylene oxide moieties is random (i.e., there is a relatively random structural distribution of at least two different moieties). Such macromonomers are hydrophilic.

In the multifunctional macromonomers of Formula I, a ratio of below about 1:9 tends to render the material crystalline, whereas a ratio of greater than about 1:1 tends to reduce the absorbency of the material. Also, the longer the alkyl group ($R^1$), the lower the absorbency of the material. Preferably $R^1$ is a C1 alkyl and the copolymeric alkylene oxide moiety is a poly(ethylene oxide-co-propylene oxide).

The multifunctionality of the material leads to crosslinking upon polymerization. Typically, the higher the molecular weight, the greater the distance between crosslinks (i.e., the lower the crosslink density), which leads to better mechanical properties. That is, the materials of the present invention possess an advantageous balance of compliance (i.e., elasticity) and tensile strength as well as cohesive strength in the swollen form as a result of the use of the multifunctional poly(alkylene oxide) macromonomer.

As stated above, the multifunctional macromonomer has a weight average molecular weight of at least about 2000. Macromonomers with molecular weights lower than this tend to form brittle polymers. Preferably the multifunctional macromonomer has a weight average molecular weight of at least about 4000, more preferably at least about 6000, and most preferably at least about 10,000. Such materials can have significantly higher molecular weights as well. Preferably, such multifunctional macromonomers have a molecular weight such that they are flowable and processable at room temperature. High molecular weight multifunctional macromonomers that are not flowable at room temperature can be used if they can be processed using diluents or other additives and/or higher temperatures (e.g., extrusion temperatures). Most preferably, useful multifunctional macromonomers are liquid at room temperature.

Herein, multifunctional means that the macromonomer has more than one reactive group that is free radically polymerizable. Preferably, there are two or three reactive groups, and more preferably two reactive groups. Such multifunctional macromonomers can be linear or branched, preferably they are linear.

Preferably, the free radically polymerizable functionality of the multifunctional macromonomer includes ethylenic unsaturation. Examples of suitable ethylenically unsaturated groups include (meth)acryloyl, (meth)acrylamido, allyloxy, vinyl, etc., as well as combinations thereof. Alternatively, the reactive groups can include photoinitiator groups. Examples of photoinitiator groups include those derived from 1-[4-(2-hydroxyethoxy)phenyl]-2-hydroxy-2-methyl-1-propane-1-one (IRGACURE 2959) or any photoinitiator with a reactive nucleophilic group, such as 4-(2-hydroxyethoxy)benzophenone.

Preferably, the multifunctional macromonomer is difunctional. A particularly preferred difunctional macromonomer is of the formula (Formula (II):

XO—(—CH($R^1$)—CH$_2$—O—)$_m$-
(—CH$_2$—CH$_2$—O—))$_n$—Y wherein: $R^1$, m, and n are as defined above; and X and Y are each independently selected from the group consisting of

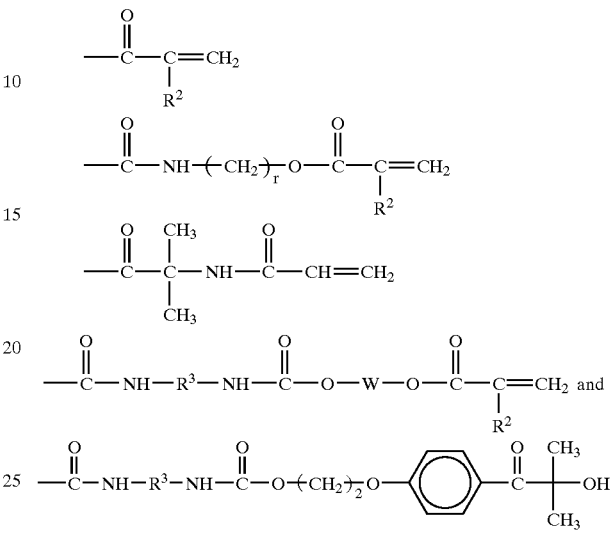

wherein $R^2$ H or CH$_3$, $R^3$ is an aromatic group, aliphatic group, alicylic group, or combinations thereof, W is an alkylene or alkylene oxide group, and r=2–10.

Preferably, the $R^3$ groups are derived from diisocyanates. More preferably, $R^3$ is selected from the group consisting of —(CH$_2$)$_p$— wherein p=1–18, tolylene, and

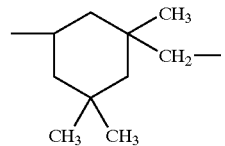

Most preferably, $R^3$ is derived from toluene diisocyanate, hexamethylene diisocyanate, or H$_{12}$-MDI (4,4'-methylene bis(cyclohexyl)diisocyanate).

Preferably, W is an alkylene or alkylene oxide containing up to 100 carbon atoms. More preferably, W is a group derived from an hydroxyalkyl (meth)acrylate.

As with Formula I, the alkylene oxide moieties of Formula II are random. More preferably, it is a random poly (ethylene oxide-co-propylene oxide)-containing macromonomer.

The multifunctional macromonomers can also be tri-, tetra-, penta-functional, etc., macromonomers. Such compounds also include a copolymeric random alkylene oxide moiety of the formula:

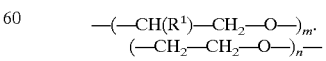

wherein the mole ratio of m:n is within a range of about 1:9 to about 9:1; and $R^1$ is a (C1–C4)alkyl group, and two or more end groups selected from the list of X and Y groups above. It should be understood that such end groups would be bonded through oxygen.

Multifunctional macromonomers can be linear with branched end groups or can be branched through a central core. Branched macromonomers can be prepared, for example, by chemical modification of linear dihydroxy terminated alkylene oxide random copolymers to produce multiple reactive end groups at each chain end. For example, a macromonomer with two polymerizable groups at each chain end can be prepared by reacting a linear dihydroxy terminated alkylene oxide random copolymer with trimellityl chloride followed by reaction with 2-hydroxyethyl methacrylate. Branch points in the macromonomer can also be introduced through incorporation of a central core. Examples of such materials include, but are not limited to, ethoxylated/propoxylated dipentaerythritol, pentaerythritol, and trimethyolpropane that have been further reacted with reactive ethylenically unsaturated compounds.

It should also be understood that each arm of a multifunctional macromonomer includes the copolymeric random alkylene oxide moiety, although each arm in any one macromonomer can be different. Also, there can be other groups or linkages, such as urethanes and/or urea groups between various copolymeric random alkylene oxide moieties in any one arm.

A particularly preferred macromonomer is of the formula

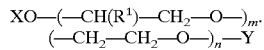

wherein $R^1$ is methyl, the mole ratio of m:n is about 1:3, and X and Y are each independently

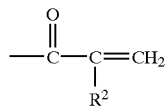

wherein $R^2$ is $CH_3$. This is referred to herein as MAA-PEG.

The functional macromonomers can be prepared, for example, by reacting dihydroxy terminated alkylene oxide random copolymers (which are typically commercially available such as poly(ethylene oxide-co-propylene oxide) commercially available as UCON-75H-90,000 from Dow Chemical Co., Midland, Mich.) with reactive ethylenically unsaturated compounds (e.g., acrylates) or photoinitiators. A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl (meth)acrylate. In addition, the dihydroxy terminated alkylene oxide random copolymer can be reacted with a diisocyanate, such as isophorone diisocyanate, resulting in an isocyanate terminated functional random copolymer that is further reacted with either functional (meth)acrylates or photoinitiators such as 2-hydroxyethyl(meth)acrylate or 1-[4-(2-hydroxyethoxy)phenyl]-2-hydroxy-2-methyl-1-propane-1-one. Preferably, the functional macromonomer is prepared by reacting the hydroxy terminated alkylene oxide random copolymer with methacrylic anhydride. Typically, if a stoichiometric amount of the ethylenically unsaturated reactant is combined with the dihydroxy terminated alkylene oxide random copolymer, 100% conversion to the disubstituted product is obtained. However, if less than a stoichiometric amount is used, the product is typically a mixture of disubstituted and monosubstituted products and possibly some dihydroxy terminated starting material. Such mixtures tend to provide gels with higher absorbency.

A multifunctional macromonomer as described herein can be homopolymerized or copolymerized with other multifunctional macromonomers or other hydrophilic monomers to enhance the absorbency of the polymer used in forming the gel material. Examples of suitable hydrophilic monomers include monofunctional poly(alkylene oxide) monomers and other polar monomers. The multifunctional macromonomer (or combination of macromonomers) can be copolymerized with hydrophobic monomers also to better control the absorbency of the polymer. Combinations of such hydrophilic and hydrophobic monomers can be used if desired.

Monofunctional poly(alkylene oxide) monomers can be used to increase the absorbency of the polymer used in forming the gel material. For certain preferred embodiments, such monomers can be analogous structurally to the multifunctional macromonomers described above with only one reactive group (e.g., only one (meth)acryloyl group, (meth) acrylamido group, allyloxy group), wherein the other end groups include nonreactive groups such as (C1–C4)alkoxy, aryloxy (e.g., phenoxy), (C1–C4)alkaryloxy, ar(C1–C4) alkyloxy, or hydroxy groups. These groups can be linear or branched.

Preferred monofunctional poly(alkylene oxide) monomers are of the formula (Formula III):

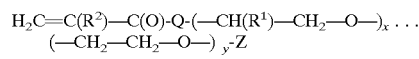

wherein the mole ratio of x:y is within a range of 0 to 1; $R^2$=H or $CH_3$; $R^1$ is as defined above for Formulas I and II; Z is H or a (C1–C4)alkyl group, an aryl group, a (C1–C4) alkaryl group, or an ar(C1–C4)alkyl group; and Q is —O—, —(H)N—C(CH$_3$)$_2$—C(O)—O—, —O—CH$_2$CH$_2$—N(H) —C(O)—O—, or

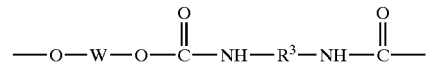

wherein $R^2$ is H or $CH_3$, $R^3$ is an aromatic group, aliphatic group, alicylic group, or combinations thereof, and W is an alkylene or alkylene oxide group. These groups can be linear or branched. As with Formulas I and II, the alkylene oxide moieties are random (unless the ratio of x:y is 0). Such materials preferably have a weight average molecular weight of at least 200. Preferred $R^3$ and W groups are as described above. Preferably, Q is oxygen.

Examples of suitable monofunctional poly(alkylene oxide) monomers include poly(ethylene oxide)(meth)acrylate, poly(propylene oxide)(meth)acrylate, poly(ethylene oxide-propylene oxide)(meth)acrylate, and combinations thereof Such monomers typically include nonreactive end groups such as (C1–C4)alkoxy, aryloxy (e.g., phenoxy), (C1–C4)alkaryloxy, ar(C1–C4) alkyloxy, or hydroxy groups. These groups can be linear or branched. These monomers can be of a wide range of molecular weights and are commercially available from sources such as Sartomer Company, Exton, Pa.; Shinnakamura Chemical Co. , Ltd. , Tokyo, Japan; Aldrich, Milwaukee, Wis.; and Osaka Organic Chemical Ind. , Ltd. , Osaka, Japan.

Polar monomers other than the poly(alkylene oxide) monomers can also be used to increase the absorbency of the polymer used in forming the gel material. Preferred polar monomers can also provide compliance to the resultant polymer. Examples of suitable polar monomers include 2-hydroxyethyl(meth)acrylate (HEMA), 2-hydroxypropyl (meth)acrylate, 3-hydroxypropyl(meth)acrylate, 4-hydroxybutyl(meth)acrylate, N-vinyl caprolactam, N-vinyl acetamide, N-vinyl pyrrolidone, acrylamide, mono- or di-N-alkyl substituted acrylamide, (meth)acrylic acid, itaconic acid, beta-carboxyethyl acrylate, glycerol methacrylate, [2-(meth) (acryloyloxy)ethyl]trimethylammonium chloride, [2-(meth) (acryloyloxy)ethyl]trimethylammonium methyl sulfate, and combinations thereof. Preferred polar monomers include 2-hydroxyethyl(meth)acrylate (HEMA) and N-vinyl pyrrolidone.

Hydrophobic monomers can be used to reduce (and thereby better control) the absorbency of the polymer used in forming the gel material, and preferably improve the strength of the polymer. Examples of suitable hydrophobic monomers include (meth)acrylic acid esters such as lauryl acrylate, 2-ethylhexyl acrylate, and isooctyl acrylate, as well as alpha-methylstyrene, and combinations thereof.

Preferred polymers used in forming the gel materials of the present invention include at least about 0.1 wt-% of the multifunctional poly(alkylene oxide) macromonomer, based on the total weight of the polymer. Practically, there is no upper limit to the amount of this multifunctional macromonomer that can be used. For example, homopolymers are possible, which could include 100 wt-% of any one multifunctional macromonomer. Preferred polymers for use in gel materials of the present invention include at least about 5 wt-% of the multifunctional poly(alkylene oxide) macromonomer, based on the total weight of the polymer. More preferably, the multifunctional poly(alkylene oxide) macromonomer is used in an amount of no greater than about 60 wt-%, based on the total weight of the polymer. Most preferably, the multifunctional poly(alkylene oxide) macromonomer is used in an amount of no greater than about 20 wt-%, based on the total weight of the polymer.

Preferred polymers used in forming the gel materials of the present invention include no greater than about 80 wt-% of a monofunctional poly(alkylene oxide) monomer, based on the total weight of the polymer. More preferably, the monofunctional poly(alkylene oxide) monomer is used in an amount of at least about 30 wt-%, based on the total weight of the polymer. Most preferably, the monofunctional poly (alkylene oxide) monomer is used in an amount of at least about 40 wt-%, based on the total weight of the polymer.

Preferred polymers used in forming the gel materials of the present invention include no greater than about 40 wt-% of a polar monomer, based on the total weight of the polymer. More preferably, the polar monomer is used in an amount of no greater than about 35 wt-%, based on the total weight of the polymer. Most preferably, the polar monomer is used in an amount of no greater than about 30 wt-%, based on the total weight of the polymer. Preferably, the polar monomer is used in an amount of at least about 5 wt-%, based on the total weight of the polymer. More preferably, the polar monomer is used in an amount of at least about 10 wt-%, based on the total weight of the polymer.

Preferred polymers used in forming the gel materials of the present invention include no greater than about 20 wt-% of a hydrophobic monomer, based on the total weight of the polymer. More preferably, the hydrophobic monomer is used in an amount of less than 20 wt-%, based on the total weight of the polymer. Even more preferably, the hydrophobic monomer is used in an amount of no greater than about 10 wt-%, based on the total weight of the polymer. Most preferably, the hydrophobic monomer is used in an amount of no greater than about 5 wt-%, based on the total weight of the polymer.

The polymer used in forming the gel material of the present invention (and preferably the gel material as well) is preferably substantially acid free. By this it is meant that no acidic monomers (e.g., (meth)acrylic acid, itaconic acid) are used in preparing the polymer in the gel material, although there may be certain acidic monomers present as contaminants in other monomers used. Thus, "substantially acid free" means that less than about 2 wt-% of the monomers used to prepare the polymer are acidic monomers.

The polymer used in forming the gel material of the present invention can be produced by polymerizing the above-described monomers by conventional polymerization methods. Typical polymerization methods that can be used include thermal and/or photochemical as well as bulk and solution polymerization.

In a typical solution polymerization method, a monomer mixture is heated with stirring in the presence of a solvent and a polymerization initiator. Examples of the solvent are methanol, ethanol, isopropanol, acetone, methyl ethyl ketone, methyl acetate, ethyl acetate, toluene, xylene, and an ethylene glycol alkyl ether. Those solvents can be used alone or as mixtures thereof. Examples of the polymerization initiator are benzoyl peroxide, cumene hydroperoxide, diisopropyl peroxydicarbonate, and azobisisobutyronitrile. Those polymerization initiators can be used alone or as mixtures thereof.

In a typical photopolymerization method, a monomer mixture is irradiated with ultraviolet (UV) rays in the presence of a photopolymerization initiator (i.e., photoinitiators). Preferred photoinitiators are those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173). Particularly preferred photoinitiators are IRGACURE 819 and 2959.

A particularly preferred method of forming the polymer is described in U.S. patent application Ser. No. 10/121,489 filed on even date herewith and entitled METHOD OF MAKING A VISCOELASTIC ARTICLE BY COATING AND CURING ON A REUSABLE SURFACE.

Preferably, the method involves a "syrup polymer" technique, by which the polymer is dissolved in the component monomers, which react into the polymer backbone, further increasing the molecular weight. Molecular weight may be controlled through the use of chain transfer agents and chain retarding agents, as are known in the art, such as alkyl mercaptans such as dodecyl mercaptan, isooctyl thioglycolate, and alpha-methylstyrene.

Thus, the present invention also provides a syrup polymer mixture and the polymerized product thereof. The syrup polymer mixture preferably includes: about 0.1 wt-% to 100 wt-% of a solute polymer having terminal or pendant reactive free-radically curable functional groups (i.e., the multifunctional poly(alkylene oxide) macromonomer described above); 0 to about 80 wt-% of a monofunctional poly(alkylene oxide) monomer; 0 to about 40 wt-% of a polar monomer (distinct from the monofunctional poly (alkylene oxide) monomer); and 0 to about 20 wt-% of a hydrophobic monomer. Such a syrup is preferably partially polymerized (typically, about 10–15% conversion) to form a coatable composition (typically, having a viscosity of about 300 centipoise to about 20,000 centipoise), then coated onto a backing or a release liner, for example, and then polymerized further to form a gel. The syrup polymer mixture preferably includes a photoinitiator. The step of forming a gel from the syrup polymer mixture preferably includes applying radiation (infrared, ultraviolet, visible, electron beam, etc., preferably, ultraviolet radiation), thermal energy, or a combination thereof (preferably sequentially).

The gel material of the present invention can include one or more active agents, such as pharmacologically active agents. Examples include, but are not limited to, growth factors (e.g., TGF, FGF, PDGF, EGF, etc.), antibacterial agents (e.g., penicillins, neomycin sulfate, sulphonamides, sulfadiazine, silver sulfadiazine, trimethoprim, and other antibiotics, as well as povidone iodine, iodine, silver, silver chloride, and chlorhexidine), antifungal agents (e.g., griseofulvin, chlormidazole hydrochloride, clotrimazole, ketoconazole, miconazole, miconazole nitrate, nistatin, and tolnaftate), disinfectants and 4 antiseptics (e.g., benzalkonium chloride, cetalkonium chloride, chlorhexidine gluconate, ethanol, iodine, methylbenzethonium, povidone iodine, isopropanol, silver, silver oxide, silver salts such as silver lactate and silver chloride, triclosan), local anaesthetics (e.g., tetracaine, benzocaine, prilocaine, procaine), debriding agents, anti-inflammatory agents (e.g., indomethacin, ketoprofen, dichlofenac, ibuprofen, etc.), astringents, enzymes, nutrients (e.g., vitamins, minerals, oxygen, etc.), drugs for cataplasms (e.g., menthol, camphor, peppermint, capsicum extract, capsaicin, etc.), and odor absorbing agents (e.g., zeolites, silicates, chitosans, cyclodextrins, etc.). Preferred active agents are antibacterial agents such as povidone iodine, iodine, silver, silver chloride, and chlorhexidine. Active agents can be used alone or as mixtures thereof. They can be added before or after the reaction product of this invention is cured as long as they do not interfere with polymerization of the polymer. Preferably, they are added in an amount or manner that does not interfere with the function or clarity of the finished gel material.

Optionally, the gel material of the present invention can include hydrocolloids, typically in the form of particles, although they are not necessarily preferred since they can diminish the transparency of the gel material. Examples of hydrocolloids include, but are not limited to, natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose) pectin, gelatin, casein and synthetic gums (polyvinylpyrrolidone, low methoxyl pectin, propyleneglycol alginates, carboxymethyl locust bean gum and carboxymethyl guar gum) and like water-swellable or hydratable hydrocolloids. The term hydrocolloid is used regardless of the state of hydration. The gel material of the present invention preferably includes an amount of the hydrocolloid such that the material is transparent (preferably, the total light transmittance is greater than 84% per ASTM D1003-00). Typically, the amount of hydrocolloid, if used, is less than about 5 wt-%, based on the total weight of the gel material.

Other additives that can be incorporated into the gel material of the present invention include: viscosity modifiers (e.g., polymeric thickeners such as that commercially available under the trade designation GANTREZ resin from International Specialty Products, Wayne, N.J.); chain transfer or retarding agents (e.g., such as alkyl mercaptans such as dodecyl mercaptan, isooctyl thioglycolate, and alpha-methylstyrene, the latter of which can also be a hydrophobic monomer as discussed above); colorants; indicators; tackifiers; plasticizers (e.g., water, glycerin, polyethylene oxide, polypropylene oxide, and mixtures thereof such as those commercially available under the trade designation PLURONICS from BASF Co., as well as various low molecular compounds capable of plasticizing the polymer); antioxidants; etc. Such additives can be added either before or after the polymerization using techniques known to one of skill in the art. Preferably, if used, they can be added in an amount and manner that does not interfere with the function or clarity of the gel material.

Preferably, the gel material of the present invention is substantially free of plasticizers, including water. This is advantageous at least because special packaging is not required. Furthermore, plasticizers can migrate to other parts of a dressing, for example, which can be detrimental to the integrity of the dressing, or into the body of the patient on which the dressing is disposed.

Optionally, the gel material may have a patterned surface on at least one major surface thereof. The patterned surface allows greater surface area for absorption of wound exudate when oriented toward the wound surface, while reducing the absorbent surface area in direct or indirect contact with the wound. More significantly, the patterned surface reduces the propensity of the absorbent layer to swell and push against the wound, avoids mushrooming (i.e. expansion of the gel layer through a porous film) and further avoids premature separation of an adhesive layer from the skin.

The optional pattern imparted to the surface of a layer of the gel material may be any suitable preselected three-dimensional pattern. Preferably, the pattern is one that increases the surface area available for absorption and reduces swelling into the wound, retards mushrooming, and/or enhances integrity of the material upon hydration. The pattern can include an array of pattern elements that include, but are not limited to, ridges, channels, mounds, peaks, hemispheres, pyramids, cylinders, cones, blocks, and truncated variations and combinations thereof. The pattern may further include apertures having a predetermined shape and size extending through the thickness of the absorbent layer.

The specific pattern element is advantageously chosen to present minimal surface area in contact with a wound or the facing film if present. The minimal surface area further retards the tendency of the gel material to swell into the wound, mushroom, or adhere to the wound site. Especially useful elements include pyramids, cones and truncated versions thereof, and ridges which are triangular in cross section. The elements may be random or non-random in the x direction, the y direction, or both. For ease of manufacture, it is preferable that the pattern comprises a non-random array of elements disposed on the surface of the gel.

If desired, a pattern may also be imparted to the outer face of the gel layer (i.e., the major surface of the gel layer that faces away from the wound surface). Imparting such a pattern increases the surface area of the gel layer and may promote greater evaporation of the fluid from the gel material. The pattern may be the same or different than the pattern on the facing surface of the gel material, as can the size of the pattern elements. Further, the individual elements on either surface of the gel material may be protuberances extending form the surface, or may be depressions in the surface.

If desired, the gel material may be in direct contact with the wound and/or skin surface. However, direct contact may be provided by other suitable hydrocolloid and hydrogel absorbent materials.

In a preferred medical article, the gel material forms a layer that is generally about 250 micrometers (i.e., microns) to about 5000 micrometers in total thickness.

Optionally, a wound dressing of the invention may include at least two absorbent layers: a first absorbent layer and a second absorbent layer. The first absorbent layer is typically more absorbent than the second absorbent layer, and can retain a greater volume of body fluids than the second absorbent layer. The second absorbent layer is positioned such that it is located between the first absorbent layer and the wound. This second absorbent layer provides integrity to the wound dressing and avoids transfer of the first absorbent layer into the wound.

The first absorbent layer typically contains the polymer described above prepared from the multifunctional macromonomer. The second absorbent layer is typically positioned in contact with the first absorbent layer and is typically less absorbent of body fluids than the first absorbent layer. The second absorbent layer can contain the reaction product of an acrylic acid ester of a non-tertiary alcohol having from 4 to 14 carbon atoms; a hydrophilic, ethylenically unsaturated monomer; and a polar, ethylenically unsaturated monomer, although other compositions can be used in the second absorbent layer.

Generally, the second absorbent layer functions as a "barrier" between the first absorbent layer (which may partially "disintegrate" when exudate is unevenly, rapidly absorbed or when it absorbs more than about 500%) and the wound. Preferably the second absorbent layer has adhesive properties (or is a pressure sensitive adhesive) and functions to enhance the overall integrity of the wound dressing. In this regard, the second absorbent layer ties the first absorbent layer to a wound-facing layer (or to the wound itself). By having adhesive properties, this second absorbent layer not only aids in controlling the absorption of exudate, but also physically joins other components of the dressing.

As stated above, the first absorbent layer is typically significantly more absorbent than the second absorbent layer, and preferably has an absorbency at least 100 percent greater than the absorbency of the second absorbent layer. The first absorbent layer preferably absorbs at least 400 percent of its weight after immersion in an isotonic saline solution after 24 hours at room temperature.

A typical wound dressing of the present invention preferably includes a porous or non-porous facing layer to provide a fluid permeable barrier between the wound site and the gel layer. The facing layer allows transport of moisture (i.e. fluid and vapor) from the wound to the gel layer and may isolate the wound from other components of the dressing. The facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims. A preferred facing layer comprises a polyurethane film.

In one useful embodiment, the facing layer is conformable to animal (including human) anatomical surfaces, has a moisture vapor transmission rate (MVTR) of at least 300 grams per square meter per 24 hours at 80% relative humidity differential at 40° C. (per method of Chen, U.S. Pat. No. 5,733,570), is impermeable to liquid water throughout substantially its entire imperforate area and contains perforations means for passing wound exudate through the facing layer. This means that the facing layer does not pass liquid water under normal wound treatment conditions except at the places in the facing layer that are positively perforated to allow the exudate to pass into the reservoir.

The preferred moisture vapor transmission rate of the facing layer is at least 600 grams per square meter per 24 hours at an 80% relative humidity differential at 40° C. The facing layer may farther comprise a pressure sensitive adhesive layer. The adhesive coated facing layer preferably has the aforesaid MVTR. Therefore, if the facing layer is impermeable to liquid water except for the perforation means, the adhesive can be permeable to liquid water and vice versa. Porous or non-porous facing layers such as perforated polyamide, polyester, polypropylene, polyethylene, polyether-amide, polyurethanes, chlorinated polyethylene, styrene/butadiene block copolymers (KRATON brand thermoplastic rubber, Shell Chemical Company, Houston, Tex.) and poly(vinyl chloride) and those described in U.S. Pat. No. 3,121,021 (Copeland) that are covered with a pressure sensitive adhesive that is not permeable to liquid water can be used for the facing layer. Optionally these films can be perforated. Additional porous materials include woven and non-woven substrates.

It is preferred that the facing layer have the above mentioned moisture vapor or liquid permeability (1) so that maceration of the skin under the wound dressing does not occur, (2) so that moisture build-up under the facing layer does not cause the facing layer and, therefore, wound dressing to be lifted off the skin, and (3) to enhance proximation of the wound edges. Preferred facing layers are thin polymeric films optionally coated with pressure sensitive adhesive which, in combination, have the above characteristics.

The perforation means in the facing layer are holes or slits or other perforations that conduct the passage of liquid water or wound exudate from the wound into the absorbent layer of the wound dressing. The perforations may additionally extend through an adhesive layer, if the front surface of the facing film (that surface facing toward the wound) is coated with a pressure sensitive adhesive layer.

A backing layer may be present in all of the embodiments of the present invention. Preferably the backing layer is conformable to animal anatomical surfaces, impermeable to liquid water and has a moisture vapor transmission rate of at least 600 grams per square meter per 24 hours at an 80% relative humidity differential at 40° C. The backing layer, in combination with a facing layer, may be constructed to form a reservoir (e.g., a pouch or envelope) that surrounds the gel layer, into which the exudate from the wound passes. This reservoir does not permit liquid water or exudate to pass out of it. Instead, the gel layer absorbs the exudate, and moisture in the exudate passes through the backing layer in a vapor form into the atmosphere. The reservoir dressing permits wound exudate to be rapidly removed from the wound site and prevents liquids or bacteria from outside the dressing to contaminate the wound site.

In order to remove moisture vapor, the moisture vapor transmission rate of the backing layer is at least as above noted, and preferably at least 1200 grams per square meter per 24 hours at an 80% relative humidity differential at 40° C.

The preferred embodiments for the facing and backing layers are thin conformable polymeric films. Generally the films are about 12 microns to about 50 microns in thickness, preferably about 12 microns to about 25 microns. Conformability is somewhat dependent on thickness, thus the thinner the film the more conformable the film. Reference has been made herein to the films utilized in the medical article (e.g., wound dressing) of the present invention being conformable to animal anatomical surfaces. This means that when the films of the present invention are applied to an animal anatomical surface, they conform to the surface even when the surface is moved. The preferred films are conformable to animal anatomical joints. When the joint is flexed and then returned to its unflexed position, the film stretches to accommodate the flexation of the joint but is resilient enough to continue to conform to the joint when the joint is returned to its unflexed condition.

Examples of films which are useful in applicant's invention as facing or backing layers include polyurethanes such as those available under the trade designation ESTANE from B. F. Goodrich, Cleveland, Ohio, elastomeric polyester such as those available under the trade designation HYTREL from E. I. duPont deNemours & Co., Wilmington, Del., blends of polyurethanes and polyesters, polyvinyl chlorides, and polyether-amide block copolymers such as those available under the trade designation PEBAX available from Elf-Atochem. Particularly preferred films for use in the present invention are polyurethane and elastomeric polyester films. The polyurethane and elastomeric polyester films exhibit a resilient property that allows the films to have good conformability.

Particularly useful films include "spyrosorbent" films having a differential moisture vapor transmission rate (MVTR). Dressings incorporating spyrosorbent films not only manage wound exudate by absorption, but have the ability to adjust the moisture vapor transmission properties in response to the amount of exudate. Such spyrosorbent films are hydrophilic, moisture vapor permeable and have a relatively high MVTR (wet), and have a differential MVTR ratio (wet to dry) that is greater than 1, and preferably greater than 3:1. The dry MVTR is greater than about 2600 g/m$^2$/24 hrs, preferably about 3000 to 4000 g/m$^2$/24 hrs. A particularly preferred spyrosorbent film, useful as a backing layer, is a segmented polyurethane such as a segmented polyether polyurethane urea based on polytetramethylene glycol and polyethylene glycol polyols. Such a spyrosorbent films are described in U.S. Pat. Nos. 5,653,699 and 4,849,458 (Reed et al.).

Another suitable backing layer is a fluid control film having at least one microstructures-bearing surface with channels that permit directional control of a liquid. This film can be used to transport a fluid to a remote site and thereby facilitate wicking away of a fluid (e.g., wound exudate). Such a film is disclosed in International Publication No. WO 00/42958.

Many different constructions of a wound dressing are possible with the facing layer, the gel layer, and the backing layer. In one embodiment, the areas of the facing layer and the backing layer are greater than that of the gel layer and the facing layer is bonded to the backing layer, thereby forming a pouch, with the gel disposed between the two. In another embodiment, one of the facing or backing layers may be substantially the same area as the gel layer, and the other of greater area. The greater area of the facing or backing layer forms a periphery to which an adhesive layer and a release liner may be attached. It will further be understood that the facing and/or backing layer may be attached or bonded to the adjacent surface of the gel layer to form a contiguous layer construction, in which the backing and facing layers may be the same or of greater area than the gel layer. Alternatively, the backing and facing layers may be bonded to each other, and may or may not be bonded to the gel layer. In these last constructions, the gel layer is constrained within a pouch created by the attachment of the facing and backing layers to each other. The layers may be bonded to each other by any conventional means such as adhesives, heat sealing, or other bonding means.

It is preferred that the facing and backing layers of the medical articles of the present invention be at least translucent and more preferably sufficiently transparent so that the wound site to which they are applied can be viewed through the medical article. It is advantageous to view and evaluate the wound and healing thereof without removal of the wound dressing to avoid unnecessary handling of the wound site and exposure of the wound to the environment, which reduces the likelihood of contamination, and avoids the need to cleanse the wound as would be the case were the dressing to be removed. It is preferred that the dressing be both transparent and colorless so that the color of the wound, exudate, and periwound skin may also be evaluated. Preferred transparent films for use as facing and backing layers that allow visual inspection of the wound site include polyurethane films such as those available under the trade designation ESTANE from B.F. Goodrich, Cleveland, Ohio; elastomeric polyesters such as those available under the trade designation HYTREL from E.I. duPont deNemours & Co., Wilmington, Del.; and, polyether block amides such as those available under the trade designation PEBAX from Elf Altochem North America, Philadelphia, Pa. Other useful films are those describes in U.S. Pat. Nos. 4,499,896 (Heinecke); 4,598,004 (Heinecke); and 5,849,325 (Heinecke et al).

While the facing layer can be attached to the wound by means other than a pressure sensitive adhesive on its surface, it is preferred to use such an adhesive. The presence of the adhesive of the facing layer normally reduces the moisture vapor permeability of the facing layer. Therefore it is preferred that the facing layer is adhesive coated prior to adding a plurality of perforations to the layer. The wound exudate therefore can readily pass through a perforated adhesive coated facing layer. Preferably, both the facing and backing layers are precoated with an adhesive layer to both facilitate bonding of the backing layer to the facing layer (forming a pouch), and bonding of the facing film to the wound site.

The facing layer is normally attached to the wound site by means of adhesive which can be continuous or pattern coated. The preferred adhesive which can be used with the wound dressings of present invention are the normal adhesives which are applied to the skin such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 that comprise block copolymers having three or more polymer block structures having a general configuration --A--B--A--- wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are acrylic adhesives such as iso-octyl acrylate/N-vinyl pyrrolidone copolymer adhesives and crosslinked acrylate adhesives such as for example those described in U.S. Pat. No. 4,112,213 (Waldman). Inclusion in the adhesive of medicaments is useful for enhancing wound healing and the inclusion of antimicrobial agents such as iodine is useful for preventing infection.

The adhesive may optionally be a microsphere adhesive with low trauma properties as described in U.S. Pat. No. 5,614,310 (Delgado et al.); a fibrous adhesive with low trauma properties as described in U.S. Pat. No. 6,171,985 B1 (Joseph et al.); or have especially good adhesion to wet skin, such as the adhesives described in U.S. Pat. No. 6,198,016 B1 (Lucast et al.), and International Publication Nos. WO 99/13866 and WO 99/13865; multilayered adhesives as disclosed in U.S. Pat. Publication No. 2001/0051178 A1 (Blatchford et al.). A particularly preferred adhesive includes 15 wt-% acrylic acid, 15 wt-% methoxypolyethylene oxide 400 acrylate, 70 wt-% isooctyl acrylate, prepared according to Example 1 of U.S. Pat. No. 5,849,325 (Heinecke et al.).

The adhesive may be chosen to be permeable to water or wound exudate, or the adhesive may be pattern coated on the front surface of the wound dressing (i.e. the surface in contact with the wound site, whether it is the front surface of the facing or backing layers) so as to not impede the flow of exudate to the gel layer, i.e. the adhesive may be coated at the periphery of the wound dressing. Alternatively the adhesive layer may be perforated as described for the facing film to provide a fluid path for the exudate.

A release liner may be attached to the adhesive layer for ease of handling. Examples of release liners are liners made of or coated with polyethylene, polypropylene and fluorocarbons and silicone coated release papers or polyester films. Examples of the silicone coated release papers are POLYS-LIK S-8004, 83 pound (135.4 g/m$^2$) bleached silicone release paper supplied by H. P. Smith Co., Chicago, Ill., and 80 pound (130.5 g/m$^2$) bleached two-sided silicone coated paper (2–80-BKG-157) supplied by Daubert Chemical Co., Dixon, Ill.

A wound dressing of the present invention may also include a frame that allows the dressing to be more easily applied to the wound. The frames are made of a relatively rigid material that maintains the shape of the dressing during handling and application to the wound site. The frame is generally releasably adhered to the back surface of the backing film and is removed after application of the wound dressing. Suitable frames are described in U.S. Pat. Nos. 5,531,855 (Heinecke et al.) and 5,738,642 (Heinecke et al.).

An optional patterned surface may be imparted to the gel material by conventional molding techniques. Alternatively, a desired pattern may be imparted using an embossing technique. Examples of such techniques are described in International Publication No. WO 01/60296 A1.

FIG. 1 shows a cross-section of a preferred wound dressing of the invention. Wound dressing 10 includes a gel layer 12 having a front surface 14 and a back surface 16. The gel layer 12 is disposed between backing layer 18 and facing layer 20. As shown, both backing layer 18 and facing layer 20 have a greater area than gel layer 12 to form a periphery 22 at which backing and facing layers may be bonded to each other. The facing layer 20 is permeable to wound exudate and preferably has a plurality of apertures 24 therethrough to conduct exudate from the wound surface to the gel layer 12. Dressing 10 may further include an adhesive layer 26 for securing dressing to the wound site. As depicted, the adhesive layer covers substantially the entire wound-facing surface of facing layer 20. In such constructions, it will be understood that the apertures would further extend though both the facing layer and the adhesive layer. It will be understood that adhesive layer 26 may be coated on only a portion of the wound dressing. For example, the adhesive layer may be coated on the periphery 22. The wound dressing 10 may further comprise a frame 28 to provide temporary support to the wound dressing during application. Frame 28, if present, is generally removably adhered to the wound dressing to facilitate removal after application of the wound dressing to the wound site.

EXAMPLES

The following examples are offered to aid in understanding of the present invention and are not to be construed as limiting the scope thereof. Unless otherwise indicated, all parts and percentages are by weight.

The following Preparative Examples are directed toward preparing macromonomers of the formula

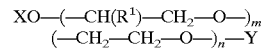

wherein X and Y are each independently selected from the group consisting of

Structure 1:

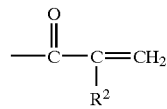

Structure 2:

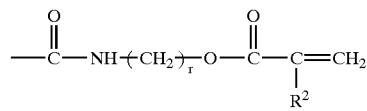

Structure 3:

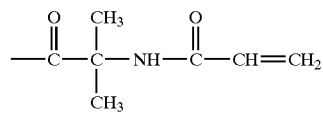

Structure 4:

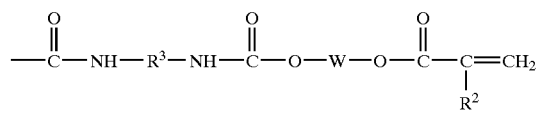

Structure 5:

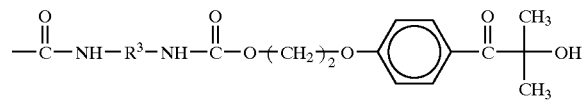

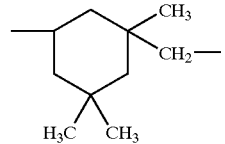

Isophorone

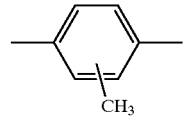

Tolylene wherein $R^1$, $R^2$, $R^3$, the mole ratio of m:n, and X and Y are as follows:

| Acronym | X | Y | $R^1$ | $R^2$ | $R^3$ | m:n | W | r |
|---|---|---|---|---|---|---|---|---|
| MAA-PEG | Structure 1 | Structure 1 | $CH_3$ | $CH_3$ | — | 1:3 | — | — |
| VAZ-PEG | Structure 3 | Structure 3 | $CH_3$ | — | — | 1:3 | — | — |
| IEM-PEG | Structure 2 | Structure 2 | $CH_3$ | $CH_3$ | — | 1:3 | — | 2 |
| IPH1-PEG | Structure 4 | Structure 4 | $CH_3$ | $CH_3$ | Isophorone | 1:3 | $(CH_2)_2$ | — |
| IPH2-PEG | Structure 4 | Structure 4 | $CH_3$ | $CH_3$ | Isophorone | 1:3 | $(CH_2)_2$ | — |
| IPH3-PEG | Structure 4 | Structure 4 | $CH_3$ | $CH_3$ | Isophorone | 1:3 | $(CH_2)_2$ | — |
| TDI-PEG | Structure 4 | Structure 4 | $CH_3$ | $CH_3$ | Tolylene | 1:3 | $(CH_2)_2$ | — |
| PIA-IPDI-PEG | Structure 5 | Structure 5 | $CH_3$ | — | Isophorone | 1:3 | — | — |

Preparative Examples

Preparation of methacrylated polyalkylene oxide (MAA-PEG). A mixture of 218.15 grams (g) of poly(ethylene oxide-co-propylene oxide) (TCON-75H-90,000, Dow Chemical Co., Midland, Mich., number average molecular weight by end group analysis of 13,228, and number average molecular by Gel Permeation Chromatography (GPC) of 24,153, and weight average molecular weigh by GPC of 25,248), 5.4 g of methacrylic anhydride (Aldrich Chemical Co., Milwaukee, Wis.), and 0.11 g of 2,6-di-tert-butyl-4-methylphenol (Aldrich Chemical Co., Milwaukee, Wis.) was heated at 100° C. under nitrogen for 12–14 hours with stirring. The product was obtained as a thick yellow liquid (abbreviated hereinafter as "MAA-PEG").

Synthesis of acrylated polyalkylene oxide (VAZ-PEG). A mixture of 3856.52 g poly(ethylene oxide-co-propylene oxide) (UCON-75H-90,000, (Dow Chemical Co., Midland, Mich.), 82.3 g of vinyl dimethyl azlactone (SNPE, Paris, France) and 1.80 g of 1,8-diazabicyclo[5.4.0]undec-7-ene (Aldrich Chemical Co., Milwaukee, Wis.) was stirred under nitrogen at room temperature for 15 minutes. The temperature was increased to 70° C. and stirring was continued for 48 hours. The product was obtained as a viscous yellow liquid (abbreviated hereinafter as "VAZ-PEG").

Synthesis of methacrylated polyalkylene oxide (IEM-PEG). A mixture of 2,497.79 g of poly(ethylene oxide-co-propylene oxide) (UCON-75H-90,000, Dow Chemical Co., Midland, Mich.), and a solution containing 1.23 g of 2,6-di-tert-butyl-4-methylphenol (Aldrich Chemical Co., Milwaukee, Wis.) in 24.69 g. of acrylic acid (Aldrich Chemical Co., Milwaukee, Wis.) was stirred at room temperature for 30 minutes. 2-Isocyanatoethylmethacrylate (59.17 g, Aldrich Chemical Co., Milwaukee, Wis.) was then added and stirring was continued for another 30 minutes, then 0.06 g of FASCAT 4224, an organotin catalyst (Atofina Chemical Co., Philadelphia, Pa.) was added and the mixture was stirred at room temperature overnight. The product was obtained as a viscous yellow liquid (abbreviated hereinafter as "IEM-PEG").

Synthesis of methacrylated urethane polyalkylene oxide (IPH1-PEG). A mixture of 606 g of poly(ethylene oxide-co-propylene oxide) (UCON-75H-90,000, Dow Chemical Co., Midland, Mich.) and a solution of 0.30 g of 2,6-di-tert-butyl-4-methylphenol (Aldrich Chemical Co., Milwaukee, Wis.) in 3.03 g of acrylic acid (Aldrich Chemical Co., Milwaukee, Wis.) was stirred under nitrogen for 30 minutes at room temperature. To this mixture 21.6 g of isophorone diisocyanate (Aldrich Chemical Co., Milwaukee, Wis.) and 0.021 g of FASCAT 4224, an organo tin catalyst (Atofina Chemical Co., Philadelphia, Pa.) were added and the mixture was heated to 65° C. with stirring. After 6 hours, 13.41 g of 2-hydroxyethyl methacrylate (Mitsubishi Rayon Co., Ltd., Tokyo, Japan) was added and heating and stirring were continued 17 hours. The product was obtained as a yellow liquid (abbreviated hereinafter as "IPH1-PEG").

Synthesis of methacrylated urethane polyalkylene oxide (IPH2-PEG). A mixture of 110.0 g of poly(ethylene oxide-co-propylene oxide) (UCON 75-H-1400, Dow Chemical Co., Midland, Mich., number average molecular by GPC of 2,265, and weight average molecular weigh by GPC of 2,378), 12.1 g of isophorone diisocyanate (Aldrich Chemical Co., Milwaukee, Wis.), 65.8 g of acetone (Aldrich Chemical Co., Milwaukee, Wis.), and 5.050 g of FASCAT 4224, an organotin catalyst (Atofina Chemical Co., Philadelphia, Pa.), was stirred under nitrogen at 55° C. After 4 hours, 2.35 g of 2-hydroxyethyl methacrylate (HEMA; Mitsubishi Rayon Co., Ltd., Tokyo, Japan), 0.050 g of 2,6-di-tert-butyl-4-methylphenol (Aldrich Chemical Co., Milwaukee, Wis.), and 0.62 g of acrylic acid (Aldrich Chemical Co., Milwaukee, Wis.) were added. After 2.5 hours at 40° C. the solution was placed under reduced pressure to remove the acetone. The product was obtained as a light yellow solution (abbreviated hereinafter as "IPH2-PEG").

Synthesis of methacrylated urethane polyalkylene oxide (IPH3-PEG). A mixture of 199.18 g of poly(ethylene oxide-co-propylene oxide) (UCON 75-H-450, Dow Chemical Co., Midland, Mich.), 52.1 g of isophorone diisocyanate (Aldrich Chemical Co., Milwaukee, Wis.), 135.3 g of acetone (Aldrich Chemical Co. , Milwaukee, Wis.), and 0.094 g of FASCAT 4224, an organotin catalyst (Atofina Chemical Co., Philadelphia, Pa.) was stirred under nitrogen at 55° C. After 24 hours, 4.72 g of 2-hydroxyethyl methacrylate (Mitsubishi Rayon Co., Ltd., Tokyo, Japan), 0.050 g of 2,6-di-tert-butyl-4-methylphenol (Aldrich Chemical Co., Milwaukee, Wis.), and 1.28 g of acrylic acid (Aldrich Chemical Co., Milwaukee, Wis.) were added. After 2.5 hours at 40° C. the solution was placed under reduced pressure to remove the acetone. The product was obtainted as a light yellow solution (abbreviated hereinafter as "IPH3-PEG").

Synthesis of methacrylated urethane polyalkylene oxide (TDI-PEG). A mixture of 100.0 g of poly(ethylene oxide-co-propylene oxide) (UCON 75-H-1400, Dow Chemical Co., Midland, Mich.), and 8.85 g of tolylene 2,4-diisocyanate (Aldrich Chemical Co., Milwaukee, Wis.) was stirred under nitrogen at 10° C. and 0.02 g of dibutyltin dilaurate (Aldrich Chemical Co., Milwaukee, Wis.) was added. The mixture warmed to 40° C. After 3 hours at 40° C., 1.24 g of 2-hydroxyethyl methacrylate (Mitsubishi Rayon Co., Ltd., Tokyo, Japan) was added and stirring was continued for one hour. The product was obtained as a thick yellow liquid (abbreviated hereinafter as "TDI-PEG").

Preparation of photoinitiator-IPDI (PIA-IPDI). To a continuously stirred solution of isophorone diisocyanate (IPDI, 5.0 g, Aldrich Chemical Co., Milwaukee, Wis.) in 50 ml $CH_2Cl_2$ under $N_2$ atmosphere was added, dropwise, a solution of IRGACURE 2959 (5 g, Ciba Specialty Chemical Corp., Tarrytown, N.Y.) and 50 mg of dibutyltin dilaurate (Aldrich Chemical Co., Milwaukee, Wis.) in 50 ml $CH_2Cl_2$. The progress of the reaction was monitored by thin layer chromatography, TLC ($CHCl_3$: $CH_3OH$, 9:1), which indicated reaction completion in 45 minutes. Solvent was removed in a rotary evaporator and the residue was washed several times with petroleum ether (Aldrich Chemical Co., Milwaukee, Wis.) until clear petroleum ether was obtained after washings. The resulting paste was dried in a rotary evaporator then in a vacuum pump for 6 hours at 35° C. to give colorless crystals. The structure of the product was confirmed by NMR analysis.

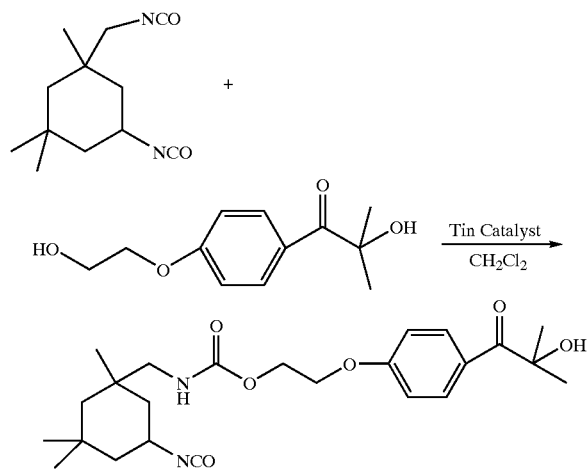

Preparation of photoinitiator containing polyalkylene oxide (PIA-IPDI-PEG). Polyalkyelene oxide (100 g, UCON-75H-90,000, Dow Chemical Co., Midland, Mich.) was dried by heating at 100° C. for 3 hours with continuous stirring and $N_2$ stream blowing through the reactor. The viscous liquid was cooled to room temperature by turning off the heat. To the viscous liquid was added PIA-IPDI (7.31 g) followed by a few drops (5–7) of dibutyltin dilaurate catalyst (Aldrich Chemical Co., Milwaukee, Wis.). Stirring at room temperature was continued overnight to give a clear liquid in quantitative yield.

Molecular Weight of Macromonomers

Molecular weight of the macromonomers was measured using Gel Permeation Chromatography (GPC). Samples were prepared by the addition of 10 milliliters (ml) of tetrahydrofuran (THF) to approximately 25 milligrams (mg) of sample. The solution was filtered using a 0.2-micron PTFE syringe filter. One hundred fifty microliters of solution was injected into a six column set (Jordi Associates mixed bed and 500 A columns, Jordi Associates Inc., Bellingham, Mass.) in combination with a Waters 2690 Separation Module (Waters Corp., Milford, Mass.), which was operated at room temperature, using THF as the eluent, flowing at a rate of 1.0 ml/min. Changes in concentration were detected by a HP 1047 A refractive index detector (Hewlett Packard Instruments, Palo Alto, Calif.). The molecular weight calculations were based upon a calibration made of narrow dispersity polystyrenes ranging in molecular weight from $6.30 \times 10^6$ to 266. The actual calculations were completed with CALIBER software (Polymer Laboratories, Inc., Amherst, Mass.) and the numbers reported are weight average molecular weights in Table 1.

TABLE 1

| Molecular Weight of Macromonomers | |
|---|---|
| Macromer | Mw |
| VAZ-PEG | 13,461 |
| IEM-PEG | 15,191 |
| IPH1-PEG | 27,201 |
| IPH2-PEG | 18,742 |
| IPH3-PEG | 34,206 |
| TDI-PEG | 20,000[a] |
| MAA-PEG | 20,216 |

[a]The TDI-PEG molecular weight was determined by NMR.

Saline Uptake

A jar was filled with 200 ml of 0.9% NaCl aqueous solution (saline). A 3-cm diameter disk of absorbent polymer with 1.1-mm thickness of polymer was weighed and recorded as "dry weight." The sample was completely submerged in the 0.9% saline and remained submerged for 24 hours at room temperature. The sample was removed, allowed to drip for 1 minute, and weighed and recorded as "wet weight." The percent uptake was calculated using the following formula:

100×(Wet weight−dry weight)/dry weight=saline uptake

Tensile Test

Tensile and elongation were measured using the following procedure. A 1.1 mm thick sample of polymer was cut into a dogbone shape approximately 75 mm long, 9 mm wide in the center, and 13 mm wide at the the ends. The sample was clamped perpendicular to the upper and lower jaws of a Thwing-Albert tensile tester. The sample is then stretched at a rate of 10 inches per minute (25.4 cm/min) until it breaks. The tensile strength is the maximum force applied to the sample at the point of break and is reported in grams per sample width. The elongation is the maximum percent stretch reached by the sample at the point of break.

Examples 1–3

Preparation of Absorbent Films

Example 1

A mixture of 99.8 g of the macromonomer MAA-PEG and 0.20 g. of IRGACURE 2959 photoinitiator (Ciba Specialty Chemical Corp., Tarrytown, N.Y.) were mixed on a roller for 24 hours then cured between two polyester release liners under UV light at a total dose of 2100 $mJ/cm^2$. The resulting polymer film was 1.1 mm thick when removed from the polyester release liners.

Example 2

Example 2 was prepared as in Example 1 with macromonomer VAZ-PEG used instead of MAA-PEG.

Example 3

Example 3 was prepared as in Example 1 with macromonomer IEM-PEG used instead of MAA-PEG.

The resulting polymeric films were tested for swelling in saline. The results for saline uptake are in Table 2. The samples remained transparent after swelling.

TABLE 2

| Example | MAA-PEG (g) | VAZ-PEG (g) | IEM-PEG (g) | IRGACURE 2959 (g) | Saline Uptake (%) |
|---|---|---|---|---|---|
| 1 | 99.8 | 0 | 0 | 0.20 | 746 |
| 2 | 0 | 99.8 | 0 | 0.20 | 740 |
| 3 | 0 | 0 | 99.8 | 0.20 | 680 |

IRGACURE 2959 from Ciba Specialty Chemical Corp., Tarrytown, NY

Examples 4–13

Preparation of Absorbent Films

Absorbent films were prepared as in Example 1 except the components listed in Table 3 below were used. These included a mixture of monomers as well as macromonomer and initiator. After swelling in saline, the resulting polymers remained transparent.

Examples 14–23

Preparation of Absorbent Films

Absorbent films were prepared as in Examples 1 except the mixtures included macromonomer IEM-PEG and the monomers and initiator listed in Table 4 below. After swelling in saline, the resulting polymers remained transparent.

Examples 24–31

Preparation of Absorbent Films

Absorbent films were prepared as in Example 1 except the components listed in Table 5 below were used. After swelling in saline, the resulting polymers remained transparent.

TABLE 3

| Example | MAA-PEG (g) | MPEG-400 (g) | Lauryl Acrylate (g) | IRGACURE 2959 (g) | α-Methylstyrene (g) | Saline Uptake (%) | Tensile (g) | Elongation (%) |
|---|---|---|---|---|---|---|---|---|
| 4 | 30.2 | 70.0 | 0 | 0.15 | 0.14 | 525 | 469 | 178 |
| 5 | 10.0 | 70.4 | 19.8 | 0.14 | 0.17 | 273 | 192 | 124 |
| 6 | 10.1 | 89.8 | 0 | 0.15 | 0.15 | 580 | 166 | 142 |
| 7 | 20.2 | 70.0 | 10.0 | 0.16 | 0.23 | 378 | 298 | 174 |
| 8 | 20.8 | 80.1 | 0 | 0.18 | 0.15 | 552 | 474 | 209 |
| 9 | 10.3 | 80.0 | 10.2 | 0.15 | 0.17 | 392 | 176 | 199 |
| 10 | 16.7 | 76.7 | 6.7 | 0.17 | 0.16 | 429 | 302 | 163 |
| 11 | 13.8 | 77.1 | 6.7 | 0.15 | 0.16 | 433 | 209 | 127 |
| 12 | 25.5 | 70.1 | 5.3 | 0.15 | 0.18 | 412 | 484 | 100 |
| 13 | 20.0 | 73.8 | 6.0 | 0.08 | 0.15 | 500 | 236 | 74 |

IRGACURE 2959 from Ciba Specialty Chemical Corp., Tarrytown, NY
Methoxypolyethylene oxide 400 acrylate (MPEG 400) from Osaka Organic Chemical Industry, Ltd., Osaka, Japan
Lauryl acrylate and α-methylstyrene from Aldrich Chemical Co., Milwaukee, WI

TABLE 4

| Example | IEM-PEG (g) | MPEG 400 (g) | Lauryl Acrylate (g) | IRGACURE 2959 (g) | α-Methylstyrene (g) | Tensile (g) | Elongation (%) |
|---|---|---|---|---|---|---|---|
| 14 | 30.0 | 69.7 | 0 | 0.15 | 0.17 | 116 | 107 |
| 15 | 9.9 | 69.8 | 19.2 | 0.15 | 0.17 | 78 | 146 |
| 16 | 10.0 | 89.2 | 0 | 0.14 | 0.16 | 70 | 102 |
| 17 | 20.0 | 70.0 | 10.3 | 0.14 | 0.14 | 120 | 171 |
| 18 | 20.0 | 80.3 | 0 | 0.14 | 0.15 | 98 | 115 |
| 19 | 10.4 | 80.2 | 10.5 | 0.15 | 0.15 | 63 | 101 |
| 20 | 16.7 | 72.5 | 6.7 | 0.14 | 0.14 | 101 | 132 |
| 21 | 13.8 | 77.0 | 6.5 | 0.14 | 0.15 | 76 | 123 |
| 22 | 25.0 | 72.2 | 5.0 | 0.14 | 0.14 | 126 | 162 |
| 23 | 20.0 | 74.1 | 6.3 | 0.14 | 0.15 | 113 | 151 |

IRGACURE 2959 from Ciba Specialty Chemical Corp., Tarrytown, NY
Methoxypolyethylene oxide 400 acrylate (MPEG 400) from Osaka Organic Chemical Industry, Ltd., Osaka, Japan
Lauryl acrylate and α-methylstyrene from Aldrich Chemical Co., Milwaukee, WI

TABLE 5

| Example | MAA-PEG (g) | MPEG 400 (g) | HEMA (g) | IRGACURE 2959 (g) | Saline Uptake (%) | Tensile (g) | Elongation (%) |
|---|---|---|---|---|---|---|---|
| 24 | 20 | 59.8 | 20 | 0.20 | 427 | 502 | 198 |
| 25 | 25 | 59.8 | 15 | 0.20 | 433 | 389 | 102 |
| 26 | 25 | 64.8 | 10 | 0.20 | 455 | 415 | 137 |
| 27 | 30 | 59.8 | 10 | 0.20 | 430 | 521 | 143 |
| 28 | 20 | 64.8 | 15 | 0.20 | 478 | 304 | 116 |

TABLE 5-continued

| Example | MAA-PEG (g) | MPEG 400 (g) | HEMA (g) | IRGACURE 2959 (g) | Saline Uptake (%) | Tensile (g) | Elongation (%) |
|---|---|---|---|---|---|---|---|
| 29 | 20 | 69.8 | 10 | 0.20 | 497 | 297 | 108 |
| 30 | 15 | 64.8 | 20 | 0.20 | 512 | 285 | 124 |
| 31 | 15 | 69.8 | 15 | 0.20 | 527 | 279 | 125 |

IRGACURE 2959 from Ciba Specialty Chemical Corp., Tarrytown, NY
Methoxypolyethylene oxide 400 acrylate (MPEG 400) from Osaka Organic Chemical Industry, Ltd., Osaka, Japan
2-hydroxyethyl methacrylate (HEMA); Mitsubishi Rayon Co., Ltd., Tokyo, Japan Example 32

To 100 g of macromonomer MAA-PEG was added, 0.15 g of 2,2'-azobis(2,4-dimethylvaleronitrile) (VAZO-52, available from duPont) and 0.1 g of 2,2'-azobis(2-methylpropionate) (available from Wako Chemicals, Osaka, Japan). The mixture was knife coated at a thickness of 1.1 mm thick between two 0.091 mm thick PET liners and heated at 80° C. for 30 minutes.

Example 33

Example 33 was prepared as in Example 32 with macromonomer IEM-PEG used instead of MAA-PEG.

The resulting polymeric films of Examples 32 and 33 were tested for swelling in saline. The results of saline uptake are in Table 6. The samples remained transparent after swelling.

TABLE 6

| Example | MAA-PEG (g) | IEM-PEG (g) | Saline Uptake (%) |
|---|---|---|---|
| 32 | 100 | — | 308 |
| 33 | — | 100 | 644 |

Example 34

A curable composition containing 36.56 parts by weight of MAA-PEG, poly(ethylene oxide-ran-propylene oxide) dimethacrylate (reaction product of UCON 75-H-90,000 (Dow Chemical Company, Midland, Mich.) with methacrylic anhydride), 38.47 parts by weight of 2-hydroxyethyl methacrylate (Mistubishi Rayon Co., Tokyo, Japan), 119.52 parts by weight of methoxypolyethylene oxide 400 acrylate (Osaka Organic Chemical Co., Osaka, Japan), 0.1 part by weight of alpha-methylstryene (Aldrich Chemical Co., Milwaukee, Wis.), 0.30 part by weight of IRGACURE 2959 (Ciba Specialty Chemicals Corp., Tarrytown, N.Y.) and 0.09 part by weight of IRGACURE 819 (Ciba Specialty Chemicals Corp., Tarrytown, N.Y.) was cured under UV lights (2800 mJ/cm$^2$) to give a clear, compliant film that was 1.1 mm thick. This film was tested for absorbency in 0.9% Saline and light transmission of hydrated samples. Transmittance and haze were measured on Example 34 before and after gamma irradiation (23–35 kGy) using a BYK-Gardner Hazeguard Plus, a sample of hydrated DUODERM SIGNAL (ConvaTec Ltd., division of Bristol-Myers Squibb, Princeton, N.J.) was measured as a comparative and the data is presented in Table 7.

TABLE 7

| Example | Saline Absorbency (%) | Transmittance (%) | Haze (%) |
|---|---|---|---|
| Example 34-before gamma irradiation | 596 | 97.5 | 1.77 |
| Example 34-after gamma irradiation | 523 | 97.5 | 1.77 |
| DUODERM SIGNAL (Comparative) | — | 62.4 | 102.0 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A medical article comprising a gel material comprising a copolymer of a difunctional poly(alkylene oxide) macromonomer, a polar monomer, a monofunctional poly(alkylene oxide) monomer, and a hydrophobic monomer, wherein the hydrophobic monomer is alpha-methylstyrene; and wherein the difunctional macromonomer has a weight average molecular weight of at least about 2000, and is of the formula:

XO—(—CH(R$^1$)—CH$_2$—O—)$_m$
(—CH$_2$—CH$_2$—O—)$_n$—Y wherein; the mole ratio of m:n is within a range of about 1:9 to about 9:1; and R$^1$ is a (C1–C4) alkyl group; and X and Y are each independently selected from the group consisting of

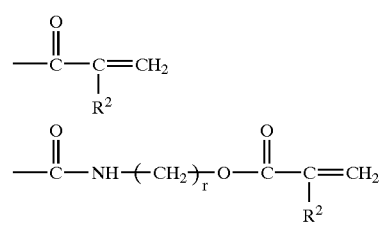

-continued

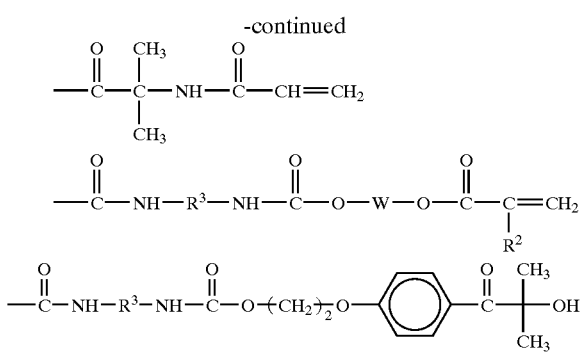

wherein $R^2$ is H or $CH_3$, $R^3$ is an aromatic group, aliphatic group, alicyclic group, or combinations thereof, W is an alkylene or alkylene oxide group, and r =2–10.

2. The medical article of claim 1 which is selected from the group consisting of a wound dressing, a wound packing, an adhesive, an adhesion preventing material, a blood purification absorbent, a base material for releasing a pharmacologic agent, a dental molding, a dental impression, a dental restorative, a dental coating, a dental composite, a dental sealant, and combinations thereof.

3. The medical article of claim 1 wherein the gel material is absorbent.

4. The medical article of claim 1 wherein $R^1$ is methyl, the mole ratio of m:n is about 1:3, and X and Y are each independently

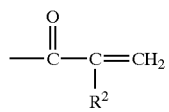

wherein $R^2$ $CH_3$.

5. The medical article of claim 1 wherein the monofunctional poly(alkylene oxide) monomer is of the formula:

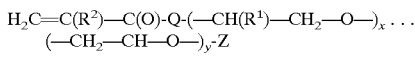

wherein the mole ratio of x:y is within a range of 0 to 1; $R^2$=H or $CH_3$ $R^1$ is a (C1–C4)alkyl group; Z is H or a (C1–C4)alkyl group, an aryl group, a (C1–C4)alkaryl group, or an ar(C1–C4alkyl) group; and Q is —O—, —(H)N—C$(CH_3)_2$—C(O)—O—, —O—$CH_2CH_2$—N(H)—C(O)—O—, or

wherein $R^2$ is H or $CH_3$, $R^3$ is an aromatic group, aliphatic group, alicyclic group, or combinations thereof, and W is an alkylene or alkylene oxide group.

6. The medical article of claim 1 wherein the polar monomer is selected from the group consisting of 2-hydroxyethyl(meth)acrylate, 2-hydroxypropyl(meth)acrylate, 3-hydroxypropyl(meth)acrylate, 4-hydroxybutyl(meth)acrylate, N-vinyl caprolactam, N-vinyl acetamide, N-vinyl pyrrolidone, acrylamide, mono- or di-N-alkyl substituted acrylamide, (meth)acrylic acid, itaconic acid, beta-carboxyethyl acrylate, glycerol methacrylate, [2(meth)(acryloyloxy)ethyl] trimethylammonium chloride, [2-(meth)(acryloyloxy)ethyl] trimethylammonium methyl sulfate, and combinations thereof.

7. The medical article of claim 1 wherein the hydrophobic monomer is a (meth)acrylic acid ester.

8. The medical article or claim 7 wherein the (meth) acrylic acid ester is selected from the group consisting of lauryl acrylate, 2ethylhexyl acrylate, isooctyl acrylate, and combinations thereof.

9. The medical article of claim 1 wherein the gel material is substantially acid free.

10. The medical article or claim 1 wherein the gel material further comprises hydrocolloid particles.

11. A medical article of claim 10 wherein the hydrocolloid particles comprise carboxymethyl cellulose particles.

12. The medical article of claim 1 wherein the gel material is transparent when dry or swollen with an aqueous solution.

13. The medical article of claim 1 further comprising a pharmacologically active agent.

14. The medical article of claim 2 which is a wound dressing or wound packing.

15. The medical article of claim 2 which is a dental impression material.

16. A medical article comprising a transparent gel material comprising a copolymer prepared from monomers comprising:
a multifunctional poly(alkylene oxide) free-radically polymerizable macromonomer having a weight avenge molecular weight of at least about 2000, wherein the multifunctional poly(alkylene oxide) macromonomer comprises a copolymeric random alkylene oxide moiety of the formula:

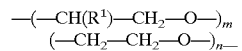

wherein the mole ratio of m:n is within a range of about 1:9 to about 9:1; and $R^1$ is a (C1–C4)alkyl group;
a monofunctional poly(alkylene oxide) monomer; and
a polar monomer.

17. The medical article of claim 16 which is a wound dressing or wound packing.

18. The medical article of claim 16 wherein the gel material is transparent and absorbent.

19. The medical article of claim 1 further comprising:
a film on which the gel material is disposed; and
a perforated film.

20. The medical article of claim 1 further comprising:
a permeable facing layer having a layer of pressure sensitive adhesive on at least a portion of the front surface of the facing layer;
a backing layer bonded to said facing layer at the periphery; and
the gel material disposed between the backing and facing layers.

21. The medical article of claim 20 wherein the backing layer is permeable to moisture vapor.

22. The medical article of claim 20 further comprising a release liner secured to the adhesive layer.

23. The medical article of claim 20 wherein the backing layer and facing layer are transparent.

24. The medical article of claim 20 wherein said adhesive is selected from acrylic adhesives.

25. A method of maintaining a moist wound healing environment, the method comprising applying the gel material of claim 1.

* * * * *

UNITED STATES PATENT AND TRADEMARK OFFICE
CERTIFICATE OF CORRECTION

PATENT NO. : 7,005,143 B2
APPLICATION NO. : 10/121518
DATED : February 28, 2006
INVENTOR(S) : Ahmed S. Abuelyaman It is certified that error appears in the above-identified patent and that said Letters Patent is hereby corrected as shown below:

Title Page
Item [75], Inventors, delete "Duane Fansler, Dresser, WI (US);"

Column 4
Line 51, delete "(–CH$_2$–CH$_2$–O–))$_n$–" and insert -- (–CH$_2$–CH$_2$–O–)$_n$– --, therefore.

Column 5
Line 16, delete "(–CH(R$^1$)–CH$_2$–O–))$_m$–" and insert -- "(–CH(R$^1$)–CH$_2$–O–)$_m$– --, therefore.
Line 64, delete "THE FIGURES" and insert -- PREFERRED EMBODIMENTS --, therefore.

Column 8
Line 2, delete "(–CH$_2$–CH$_2$–O–))$_n$–Y" and insert -- (–CH$_2$–CH$_2$–O–)$_n$–Y --, therefore.
Line 30, after "R$^2$" insert -- is --.

Column 10
Line 54, after "thereof" insert -- . --.

Column 12
Line 45, after "10/121,489" insert -- . --.

Column 13
Line 22, after "and" delete "4".

UNITED STATES PATENT AND TRADEMARK OFFICE
CERTIFICATE OF CORRECTION

PATENT NO. : 7,005,143 B2
APPLICATION NO. : 10/121518
DATED : February 28, 2006
INVENTOR(S) : Ahmed S. Abuelyaman It is certified that error appears in the above-identified patent and that said Letters Patent is hereby corrected as shown below:

Column 16
Line 13, delete "farther" and insert -- further --, therefore.

Signed and Sealed this

Sixth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,005,143 B2
APPLICATION NO. : 10/121518
DATED : February 28, 2006
INVENTOR(S) : Ahmed S. Abuelyaman It is certified that error appears in the above-identified patent and that said Letters Patent is hereby corrected as shown below:

Title Page
Item [75], Inventors, delete "Duane Fansler, Dresser, WI (US);"

Column 4
Line 51, delete "$(-CH_2-CH_2-O-))_n-$" and insert -- $(-CH_2-CH_2-O-)_n-$ --, therefore.

Column 5
Line 16, delete "$(-CH(R^1)-CH_2-O-))_m-$" and insert -- "$(-CH(R^1)-CH_2-O-)_m-$ --, therefore.
Line 64, delete "THE FIGURES" and insert -- PREFERRED EMBODIMENTS --, therefore.

Column 8
Line 2, delete "$(-CH_2-CH_2-O-))_n-Y$" and insert -- $(-CH_2-CH_2-O-)_n-Y$ --, therefore.
Line 30, after "$R^2$" insert -- is --.

Column 10
Line 54, after "thereof" insert -- . --.

Column 12
Line 45, after "10/121,489" insert -- . --.

Column 13
Line 22, after "and" delete "4".

Column 16
Line 13, delete "farther" and insert -- further --, therefore.

Column 21
Line 22, delete "(TCON" and insert -- (UCON --, therefor.

Column 29
Line 40, after "$R^2$" insert -- is --.
Line 44, delete "$(-CH_2-CH-O-)_y-Z$" and insert -- $(-CH_2-CH_2-O-)_y-Z$ --, therefore.
Line 46, delete "$CH_3R^1$" and insert -- $CH_3; R^1$ --, therefore.
Line 48, delete "(C1-C4alkyl" and insert -- (C1-C4)alkyl --, therefore.

UNITED STATES PATENT AND TRADEMARK OFFICE
CERTIFICATE OF CORRECTION

PATENT NO. : 7,005,143 B2
APPLICATION NO. : 10/121518
DATED : February 28, 2006
INVENTOR(S) : Ahmed S. Abuelyaman It is certified that error appears in the above-identified patent and that said Letters Patent is hereby corrected as shown below:

Column 30
Line 1, delete "[2(meth)(acryloyloxy)ethyl]" and insert
-- [2-(meth)(acryloyloxy)ethyl] --, therefore.
Line 7, delete "or" and insert -- of --, therefore.
Line 9, delete "2ethylhexyl" and insert -- 2-ethylhexyl --, therefore.
Line 13, delete "or" and insert -- of --, therefore.
Line 28, delete "avenge" and insert -- average --, therefore.

This certificate supersedes the Certificate of Correction issued May 6, 2008.

Signed and Sealed this

Twenty-second Day of July, 2008

JON W. DUDAS
*Director of the United States Patent and Trademark Office*